US00PP31147P3

(12) United States Plant Patent
Cain

(10) Patent No.: US PP31,147 P3
(45) Date of Patent: Dec. 3, 2019

(54) GRAPEVINE PLANT NAMED 'IFG THIRTY-TWO'

(50) Latin Name: *Vitis vinifera*
Varietal Denomination: IFG Thirty-two

(71) Applicant: David Cain, Bakersfield, CA (US)

(72) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 130 days.

(21) Appl. No.: 15/732,689

(22) Filed: Dec. 15, 2017

(65) Prior Publication Data

US 2019/0191612 P1 Jun. 20, 2019

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 6/88; A01H 5/08
See application file for complete search history.

*Primary Examiner* — Keith O. Robinson

(57) ABSTRACT

This invention is a new and distinct grapevine variety denominated 'IFG Thirty-two'. The new grapevine plant is characterized by producing medium size finger shaped berries having medium firm texture with a neutral flavor and which ripen in mid-season. Berries are borne on medium size clusters which are naturally loose and do not require gibberellin applications to thin clusters.

1 Drawing Sheet

Latin name of the genus and species claimed: *Vitis vinifera.*

Variety denomination: 'IFG Thirty-two'.

BACKGROUND OF THE INVENTION

The new and distinct grapevine plant described and claimed herein originated from a hand pollinated cross of IFG 02091-099-298 (unpatented), a seedless selection from the IFG breeding program and 01159-bulk (unpatented), a bulked pollen from several unnamed siblings from the IFG breeding program hybridized in May 2005. The abortive seed traces were subsequently embryo cultured and the resulting 149 plants were planted in the field in April 2006. The present variety of grapevine was selected as a single plant in October 2008 and was first asexually propagated by hardwood cuttings in December 2008 near Delano, Kern County, Calif. The resulting propagules were planted during April 2009 near Delano, Kern County, Calif. and were found to reproduce true-to-type through at least two generations of asexual reproduction.

BRIEF SUMMARY OF THE INVENTION

The new grapevine 'IFG Thirty-two' is characterized by producing medium size finger shaped berries having medium firm texture with a neutral flavor and which ripen in mid-season. Berries are borne on medium size clusters which are naturally loose and do not require gibberellin applications to thin clusters. Berry size can be increased by applying gibberellic acid. Berries store well and retain their condition for up to eight weeks in cold storage. To the inventor's knowledge, the known variety to which the new grapevine variety is most similar is the Centennial Seedless variety (Table grape; U.S. Plant Pat. No. 4,784). 'IFG Thirty-two' differs from 'Centennial Seedless' by having smaller berry size, firmer berries, with a narrower, more tapered finger shaped, lighter green skin color and better storage ability.

'IFG Thirty-two' differs from its maternal parent: 'IFG 02091-099-298' (unpatented seedling selection in the IFG breeding program) by having a narrower cylindrical to fingered shape berry shape and having a smaller berry size. The pollen parent of 'IFG Thirty-two' is a composite of several similar red/black skinned elliptic to ovate selections from the 01159 progeny which were bulked together and used to pollinate 'IFG 02091-099-298'. 'IFG Thirty-two' can be distinguished from any of the selections in the bulked pollen by ripening earlier and having, Yellow-green rather than red or black skin color and having a narrower, more elongated finger shape.

BRIEF DESCRIPTION OF THE DRAWING

The accompanying photographic drawing in FIG. 1 illustrates in full color 'IFG Thirty-two', taken from a 4-year-old vine. The photograph was taken outdoors with indirect lighting. The colors are as nearly true as is reasonably possible in a color representation of this type. The left side of the drawing has mature leaves. A mature fruit cluster is represented in the center of the drawing along with a typical berry in cross section. A young shoot can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Thirty-two' plants grown in the vicinity of Delano, Kern County, Calif. during 2015 and 2016, and is believed to apply to plants of the variety grown under similar conditions of soil and climate elsewhere:

Vine:

*General.*—Vigor — Moderate. Density of foliage — Dense. Productivity — Very productive, producing about 32.2 to 48.4 kg of fruit per vine. Root stock — Own root. Training method — Typically spur pruned leaving 2 bud spurs.

*Trunk.*—Trunk diameter of 4-year-old vines at 30 cm above the soil line — About 6.7 cm. Size — Moderately stocky. Straps — Short, split. Surface texture — Medium rough texture. Inner bark color — Greyed-orange: 165A.

Shoots:

*Young shoot.*—Form of tip — Wide open. Distribution of anthocyanin coloration of tip — Absent. Intensity of anthocyanin coloration of tip — Absent. Density of prostrate hairs of tip — Sparse. Density of erect hairs on tip — Absent. Color — Yellow-green: 144A.

*Woody shoot* (*mature canes*).—Internode length — Medium-long: About 15.0 cm. Width at node — About 1.4 cm. Cross section — Circular. Surface — Striate. Main color — The following colors were observed: Greyed-orange 165B and 166A. Density of erect hairs on nodes — None or very sparse. Density of erect hairs on internodes — None or very sparse. Axillary shoot length at full bloom — Weak: approximately 5.2 cm.

*Flowering shoot.*—Vigor during flowering — Strong. Attitude during flowering on shoots not tied — Semi-erect. Color — dorsal side of internodes — Yellow-green: 146C, with Red-purple stripes: 59B. Color — ventral side of internodes — Yellow-green: 146C. Color — dorsal side of nodes — Yellow-green: 146C, with Red-purple stripes: 59B. Color — ventral side of nodes — Yellow-green: 146C. Density of prostrate hairs on nodes — Very sparse. Density of erect hairs on nodes — None. Density of prostrate hairs on internode — Very sparse. Density of erect hairs on internode — None. Anthocyanin coloration of buds — Present.

*Tendrils.*—Distribution on the shoot (at full flowering) — Discontinuous. Length of Tendril — Long: About 22.9 cm. Thickness of tendril 2 cm from base — About 2.8 mm. Color — The following colors were observed: Yellow-green: 144B and N144A. Form — Bifurcated. Number of consecutive tendrils — 2.

Leaves:

*Young leaves.*—Color of upper surface of first four distal unfolded leaves — Yellow-green: 146A. Average intensity of anthocyanin coloration of six distal leaves prior to flowering — Very weak. Density of prostrate hairs between veins (lower surface) — Very sparse. Density of prostrate hairs on veins (lower surface) — Very sparse. Density of erect hairs between veins (lower surface) — Absent. Density of erect hairs on veins (lower surface) — Sparse.

*Mature leaves.*—Average length — About 13.8 cm. Average width — About 16.8 cm. Mature leaf size — Medium. Shape of blade — Wedge shaped. Number of lobes — 5. Blade venation — Palmate. Anthocyanin coloration of main veins on upper side of blade — Very weak. Mature leaf profile — Flat. Blistering surface of blade upper surface — Weak. Leaf blade tip — In the plane of the leaf. Undulation of margin — Slight. Undulation of blade between main and lateral veins — Absent. Shape of teeth — Mixture of both sides straight and both sides convex. Length of teeth — Long: Approximately 1.1 cm. Ratio length/width of teeth — Medium. Shape of upper lateral sinuses — Lobes slightly overlapping. Depth of upper lateral sinuses — Deep. General shape petiole sinus — Wide open. Shape of base of upper leaf sinuses — U-shaped. Tooth at petiole sinus — Absent. Density of prostrate hairs between veins on lower surface of blade — Very sparse. Density of erect hairs between veins on lower surface of blade — Very sparse. Density of prostrate hairs on main veins on lower surface of blade — Very sparse. Density of erect hairs on main veins on lower surface of blade — Sparse to medium. Density of prostrate hairs on main veins on upper surface of blade — None or very sparse. Density of erect hairs on main veins on upper surface of blade — None. Autumn coloration of leaves — Leaves can be a single color or combination of colors, in a mottled pattern or on the edges of the leaves. The following colors were observed: Greyed-yellow: 162A and 162B.

*Upper surface.*—Color — The following colors were observed: Green: 137A and 137B. Anthocyanin coloration of main veins (lower surface) — Very weak. Color of main veins — Yellow-green: 144C. Surface appearance — Semi-glossy. Texture: blistering surface of blade — Weak.

*Lower surface.*—Color — The following colors were observed: Yellow-green: 146A and 146B. Anthocyanin coloration of main veins (lower surface) — Weak. Color of main veins — Yellow-green: 145C. Glossiness — Medium. Surface texture — Rugose. Surface appearance — Semi-glossy.

*Petiole.*—Length — About 10.3 cm. Diameter of petiole 2 cm from base — About 3.7 mm. Petiole color — The following colors were observed: Yellow-green: 145A and 145B and Greyed-purple: 186B. Length of petiole compared to middle vein — Slightly shorter. Density of prostrate hairs on petiole — Very sparse. Density of erect hairs on petiole — None.

*Buds.*—Bud fruitfulness — Basal: mostly fruitful. Position of first fruitful shoot on previous season cane — $1^{st}$ to $2^{nd}$ node. Dormant bud length — About 5.9 mm. Dormant bud width in the proximal/distal plane — About 6.8 mm. Dormant bud color —

Greyed-orange: 166A. Time of bud burst — Mid-season: About Mar. 6, 2015.

Flowers:

*General.*—Flower sex — Hermaphrodite. Length of first inflorescence — Medium: About 15.7 cm long by 8.5 cm wide. Position of first flowering and fruiting node — $3^{rd}$ node (current season growth). Number of inflorescence per flowering shoot — 1.1 to 2: About 1.8. Time of bloom — Medium as compared with similar varieties in the growing area of Delano, Calif. Date of full bloom — About Apr. 29, 2015.

Fruit:

*General.*—Ripening period — Mid-season: Approximately 8-13-15. Use — Fresh market. Keeping quality — Good, remains commercially acceptable when stored up to 8 weeks at 0° C. and high relative humidity. Resistance to — Insects: Average typical of *Vitis vinifera* species. Diseases: Average typical of *Vitis vinifera* species. Refractometer test — Soluble solids: about 20.0 Brix. Brix/Acid — About 40.8. Titratable acidity — About 0.49. Juice pH — About 3.66.

*Cluster.*—Mature cluster length (peduncle excluded) — About 22.6 cm. Mature cluster width — About 20.5 cm. Mature cluster weight — About 1076 g. Bunch density — Loose to medium. Number of berries — About 264. Form — Conical.

*Peduncle.*—Lignification of peduncle — Weak. Length of peduncle — Medium: approximately 3.5 cm.

*Berry.*—Uniformity of size — Uniform. Single berry weight — About 5.9 g natural. Shape — Range of cylindrical and finger-shaped berries, few have horn-shaped appearance. Seeds — Absent. Cross section — Circular. Berry dimensions — Longitudinal axis: about 41.9 mm: horizontal axis: about 14.8 mm. Berry firmness — Medium. Particular flavor — Neutral. Bloom (cuticular wax) — Weak. Berry separation from pedicel — Moderate to somewhat easy. Skin color (without bloom) — The following colors were observed: Yellow-green: 145B and 145C. Flesh color — Green-white: 157C. Anthocyanin coloration of flesh — Absent.

*Skin.*—Thickness — Medium. Skin toughness — Not notable when chewing. Reticulation — Absent. Tenacity — Tenacious to flesh.

What is claimed:

1. A new and distinct variety of grapevine plant as herein illustrated and described.

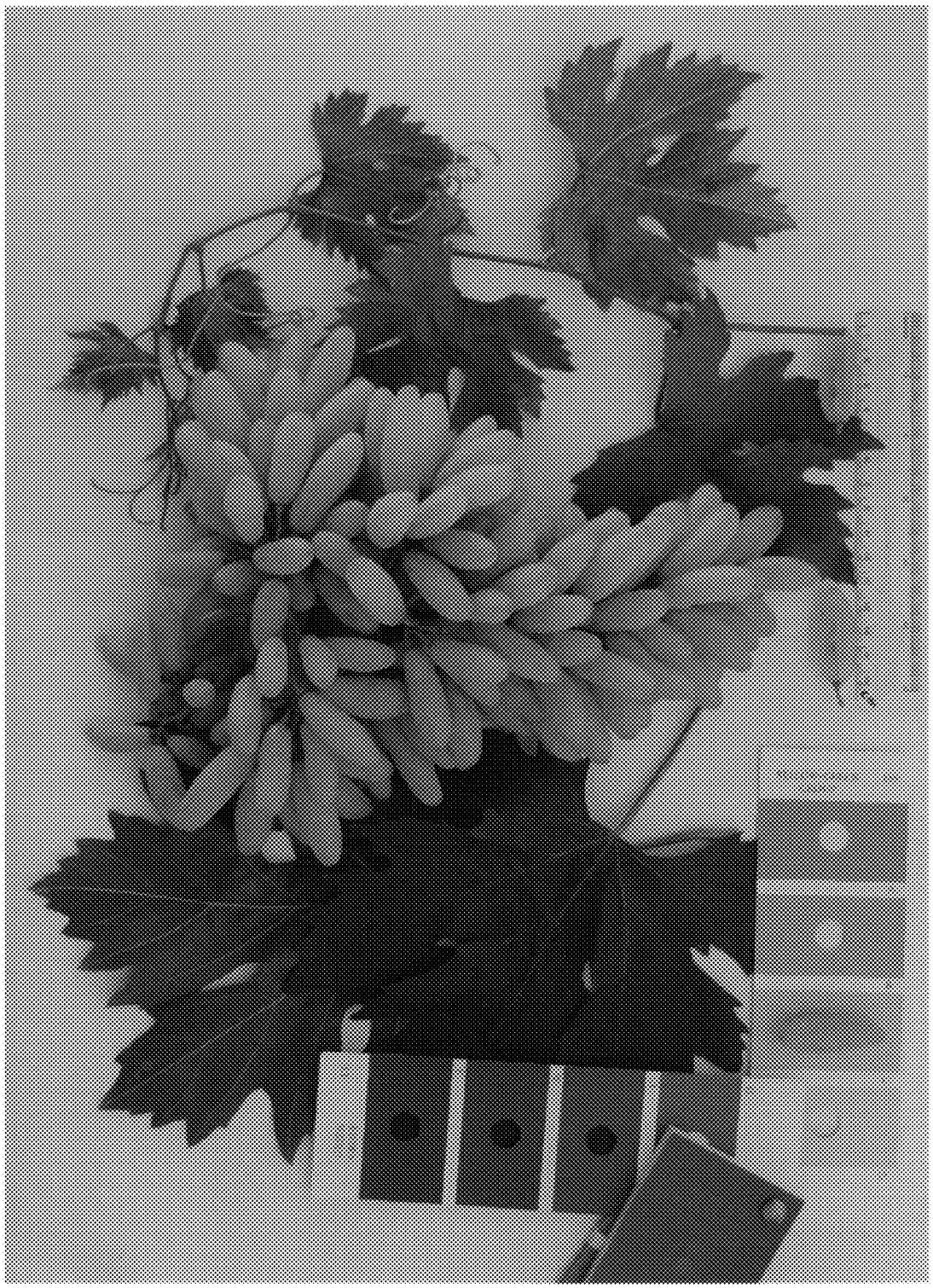

* * * * *